United States Patent [19]

Graves et al.

[11] 4,138,891

[45] Feb. 13, 1979

[54] SAMPLING OF TOXIC GASES FROM OIL AND/OR GAS WELLS

[76] Inventors: Phillip H. Graves, P.O. Box 6564; Don L. Dyer, 2905 Eastover, both of Odessa, Tex. 79762

[21] Appl. No.: 788,900

[22] Filed: Apr. 19, 1977

[51] Int. Cl.² ............................................. G01N 1/22
[52] U.S. Cl. ............................................. 73/421.5 R
[58] Field of Search .................. 73/421.5 R, 421.5 A, 73/19, 23

[56] References Cited

U.S. PATENT DOCUMENTS 2,556,832  6/1951  Vollrath .................................. 73/27
3,757,583  5/1973  Ludewig ............................. 73/421.5

FOREIGN PATENT DOCUMENTS 703079  1/1954  United Kingdom ............... 73/421.5 R Primary Examiner—S. Clement Swisher

[57] ABSTRACT

Toxic gases from oil and gas wells are sampled by a gas sensing assembly arranged at a distance from a wellhead being monitored. A gas pickup device arranged adjacent the wellhead is connected to the gas sensing assembly by a feed line through which gas is drawn from the pickup device to the gas sensing assembly by a suction pump system.

2 Claims, 2 Drawing Figures

SAMPLING OF TOXIC GASES FROM OIL AND/OR GAS WELLS

BACKGROUND OF THE INVENTION

1. Field of the Invention

This invention relates generally to the continuous monitoring of toxic gases, and particularly to the monitoring of gases adjacent a wellhead during the drilling and working over of oil and gas wells, and the like.

2. Description of the Prior Art

A serious problem associated with the drilling and working of oil and gas wells, and the like, arises from the toxic gases, such as hydrogen sulfide, emitted from such wells. Many deaths have occurred from these toxic gases during the drilling and working of oil and gas wells, and consequently the Texas Railroad Commission has passed a new rule that requires gas monitoring during the drilling and working of wells.

Various gas warning systems are available for accomplishing such gas monitoring. A disadvantage to these known systems, however, is that they must be located at the wellhead, and due to the water, mud, and other forms of contaminates found around these wells, these expensive sensing units become inoperative.

U.S. Pat. Nos. 2,210,548, issued Aug. 6, 1940, to G. L. Hassler, and 3,343,421, issued Sept. 26, 1967, to N. L. Miller, disclose soil gas sampling methods and apparatuses wherein gas is drawn by use of a vacuum into a sampling chamber disposed at a distance from the soil being sampled, while U.S. Pat. Nos. 3,641,821, issued Feb. 15, 1972, to E. D. Neuberger; 3,685,345, issued Aug. 22, 1972, to H. L. Wise; and 3,903,745, issued Sept. 9, 1975, to C. M. Bolser, disclose further examples of gas sampling systems.

SUMMARY OF THE INVENTION

It is an object of the present invention to provide for a system of sampling toxic gases from oil and/or gas wells wherein the sensing unit is disposed at a substantial distance from the wellhead.

It is another object of the present invention to provide for a gas sampling system which is simple and rugged of construction, yet reliable and efficient of operation.

These and other objects of the present invention are achieved by providing apparatus for sampling of toxic gases from oil and gas wells having: a gas sensing assembly arrangeable remotely of a wellhead; a gas pickup device arrangeable immediately adjacent the wellhead; a feed line connecting the pickup device to the gas sensing assembly; and a pump disposed for passing gas through the line from the pickup device to the gas sensing assembly. The pump advantageously includes a compressed gas line communicating with the path of a flow of gas through the feed line for creating a suction through the feed line and drawing the gas from the pickup device to the gas sensing assembly.

The gas sensing assembly preferably includes a hermetically sealed housing and a gas sensor disposed within the housing. The latter is provided with an inlet opening receiving the feed line, and with an outlet opening spaced from the inlet opening so as to create a flow path through the housing and over the gas sensor disposed within the housing. The compressed gas line has a discharge end arranged adjacent the outlet opening of the housing for creating a vacuum within the housing itself, which vacuum causes the gases to be drawn through the feed line from the pickup device to the gas sensor.

The gas sensing assembly further includes a nozzle mounted on and arranged extending from the housing so as to surround the outlet opening with the discharge end of the compressed gas line being arranged in and extending coaxially with the nozzle for creating the requisite suction to cause flow of gases being sampled through the feed line from the pickup device to the housing.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
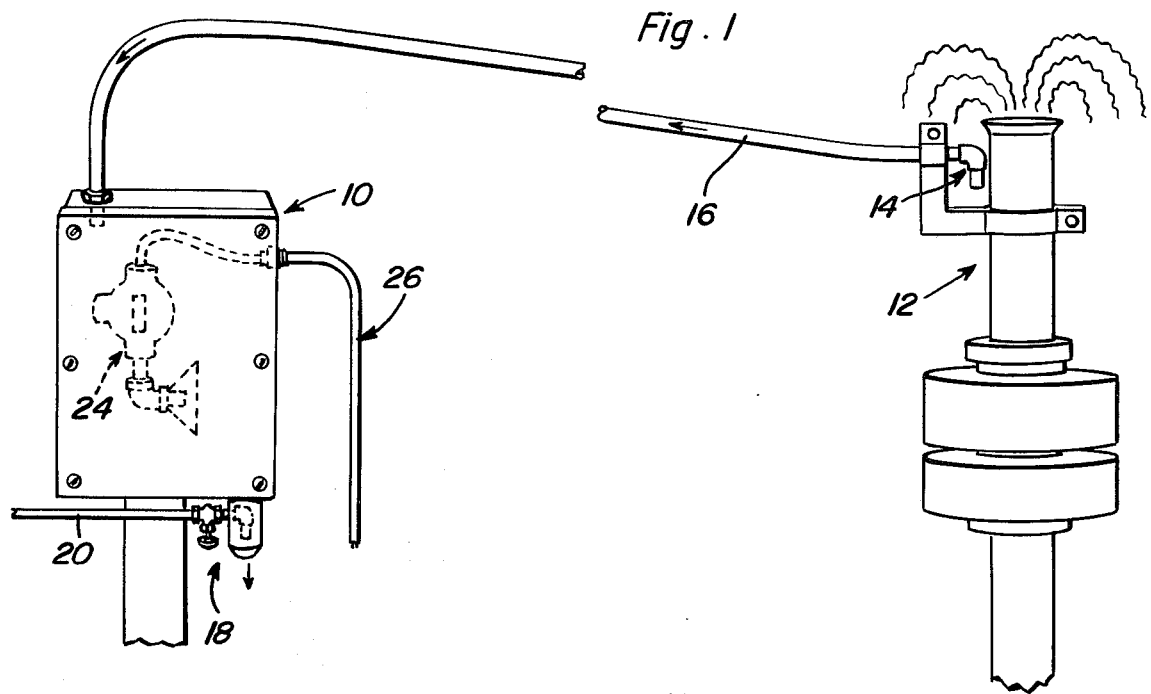
FIG. 1 is a fragmentary, perspective view showing a gas sampling system according to the present invention.
Figure 2:
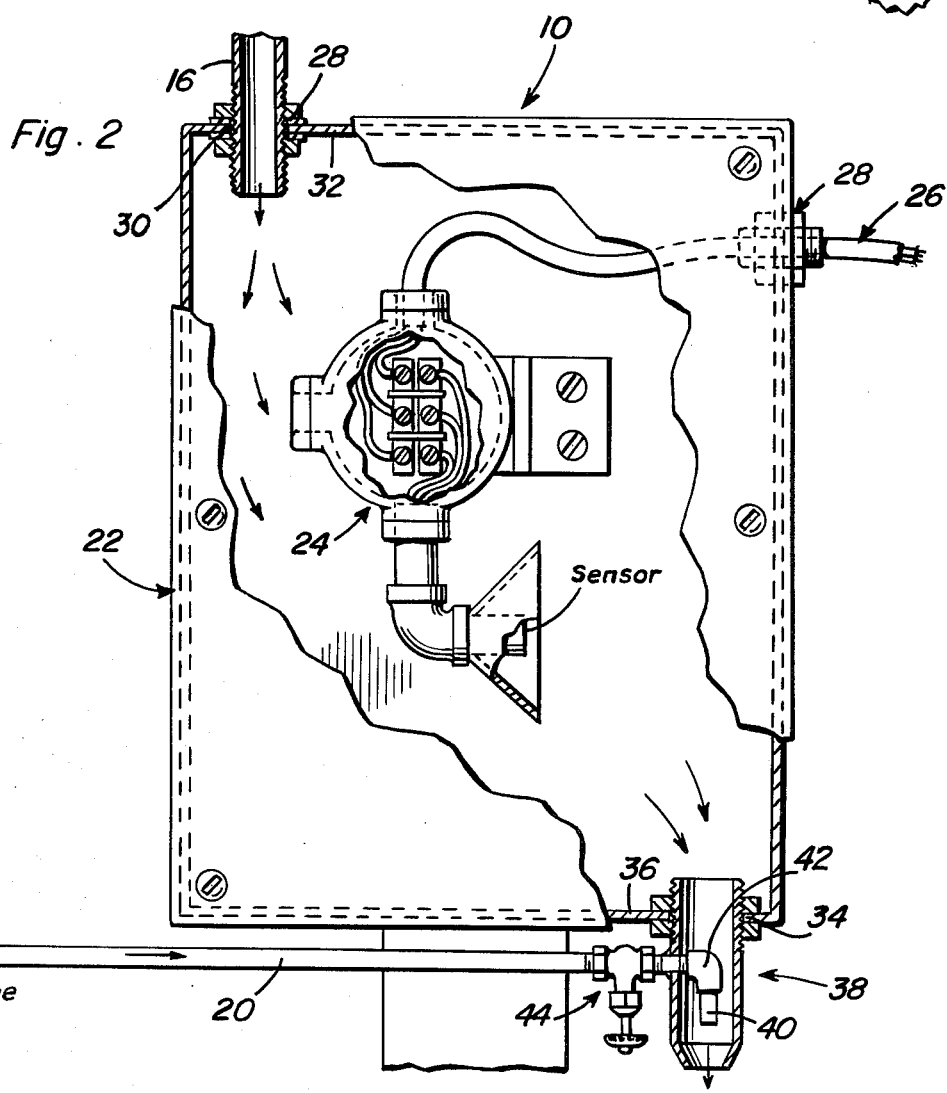
FIG. 2 is an enlarged, fragmentary, side elevational view, partly broken away and in section, showing in detail the left hand portion of FIG. 1.

Referring more particularly to the figures of the drawing, apparatus according to the invention for sampling of toxic gases from oil and gas wells, and the like, includes a gas sensing assembly 10 arrangeable remote of a wellhead 12 of conventional construction. A suitable gas pickup device 14, known per se, is mounted on wellhead 12 as by a suitable bracket so as to be immediately adjacent wellhead 12. Connected to pickup device 14 and to the gas sensing assembly 10 is a feed line 16 through which gas is caused to pass from the vicinity of wellhead 12 to the gas sensing assembly 10 by means of a pump arrangement 18.

Pump arrangement 18 includes a compressed gas line 20 communicating with the path of the flow of gases through feed line 16, and gas sensing assembly 10, for creating a suction through feed line 16 and drawing the gas from pickup device 14 to gas sensing assembly 10.

Gas sensing assembly 10 includes a hermetically sealed housing 22 and a gas sensor 24 disposed within housing 22. The gas sensor 24 is preferably mounted within housing 22 as by the illustrated bracket so as to be arranged substantially centrally of the interior of housing 22. Wires 26 extend from gas sensor 24, which may be a conventional commercially available unit, such as the "Bullard" model 9932 gas sensor, to an alarm system, not shown, of a conventional nature, as well as to suitable, known indicating and recording devices, also not shown. Since the gas sensor 24 is to be of conventional construction, it will not be described in detail herein.

Housing 22 is provided with an inlet opening 30 and a top wall 32 thereof, and with an outlet opening 34 in a bottom wall 36. Compressed gas line 20 has a discharge thereof arranged adjacent the outlet opening 34 so as to create a vacuum within the airtight, as well as waterproof, housing 22.

Gas sensing assembly 10 further includes a nozzle assembly 38 mounted on and extending away from bottom wall 36 of housing 22 so as to surround the outlet opening 34, with the discharge end 40 of compressed gas line 20 being arranged inside of and extending coaxially with the longitudinal extent of nozzle assembly 38 from a suitable elbow 42 permitting discharge end 40 to be at right angles with respect to line 20. The discharge end 40 is directed toward the throat of nozzle assembly 38 so as to create a suction within the nozzle assembly 38 and, consequently, a vacuum within housing 22. A suitable needle valve 44 is disposed within line 20 to facilitate control of pump arrangement 18.

In operation, apparatus according to the present invention is used by first locating the gas sensing assembly 10 remotely of a wellhead 12 being sampled, running line 16 from wellhead 12, or more specifically pickup device 14, to the gas sensing assembly 10, and passing gas through line 16 from immediately adjacent the wellhead 12 to the gas sensing assembly 14 by suitable actuation of pump arrangement 18. More specifically, gas is passed to the gas sensing assembly 10 by creating at outlet opening 34 of housing 22 a suction which draws gas from the wellhead 12 through housing 22 and over the gas sensor 24. Thus, when needle valve 44, or alternatively a variable-flow nozzle (not shown) mounted on discharge end 40 is opened, there is created a vacuum inside the sealed box forming housing 22 and the gas is pulled from the wellhead 12 to the sensor 24, which in turn will set off an alarm (not shown) connected to wires 26 letting crewmen know there are toxic gases escaping from the well and permitting the crew to take action to control such escaping toxic gases.

As can be readily understood from the above description and from the drawings, a toxic gas sampling system according to the present invention permits in a simple and efficient, yet rugged and reliable, manner the continuous monitoring of oil and gas wells, both during the drilling and production of such wells, in order to assure that dangerous levels of toxic gases do not endanger the lives of crewmen working on the well.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. Apparatus for sampling of toxic gases from oil and gas wells, comprising, in combination:
    (a) a gas sensing assembly arrangeable remotely of a wellhead emitting gases to be sampled;
    (b) a gas pickup device arrangeable immediately adjacent the wellhead;
    (c) a feed line connecting the pickup device to the gas sensing assembly; and
    (d) pump means for drawing gas through the line from the pickup device to the gas sensing assembly, the pump means including a compressed gas line communicating with the flow of gas through the feed line for creating a suction through the feed line and drawing the gas from the pickup device to the gas sensing assembly, the gas sensing assembly including a hermetically sealed housing and a gas sensor disposed centrally within the housing, the housing having a diameter substantially larger than the line from the pickup device and an interior substantially larger than the gas sensor, and being provided with an inlet opening receiving the feed line and with an outlet opening spaced opposite of and offset from the inlet opening so as to form a gas flow path within the housing between the inlet opening and the outlet opening and over the gas sensor the gas sensor being disposed within the housing substantially centrally of the interior of the housing, the gas sensor including a sensor arranged closest to the outlet opening, with the compressed gas line having a discharge and arranged adjacent the outlet opening provided in the housing.

2. Apparatus as defined in claim 1, wherein the pump means further includes a nozzle having a throat and arranged mounted on and extending away from the housing so as to surround the outlet opening, with the discharge end of the compressed gas line being arranged at a right angle with respect to the line and disposed in and extending coaxially with a flow path of the nozzle and toward the throat of the nozzle.

* * * * *